(12) United States Patent
Korpan et al.

(10) Patent No.: US 6,565,556 B1
(45) Date of Patent: May 20, 2003

(54) DEVICE FOR CARRYING OUT CRYOSURGICAL INTERVENTIONS, ESPECIALLY FOR TREATING TUMORS

(76) Inventors: Nikolai Korpan, Kaasgrabengasse 52/3/5, A-1190, Vienna (AT); Jaroslav Zharkov, A/c 376/7, Kiew 252146 Ukraine (UA)

( * ) Notice: Subject to any disclaimer, the term of this patent is extended or adjusted under 35 U.S.C. 154(b) by 0 days.

(21) Appl. No.: 09/673,129
(22) PCT Filed: Feb. 4, 2000
(86) PCT No.: PCT/AT00/00025
§ 371 (c)(1), (2), (4) Date: Oct. 11, 2000
(87) PCT Pub. No.: WO00/47121
PCT Pub. Date: Aug. 17, 2000

(30) Foreign Application Priority Data

| Feb. 12, 1999 | (AT) | 203/99 |
| Mar. 29, 1999 | (AT) | 571/99 |
| Apr. 27, 1999 | (AT) | 741/99 |
| Apr. 28, 1999 | (AT) | 753/99 |
| Apr. 29, 1999 | (AT) | 767/99 |

(51) Int. Cl.[7] ............................................. A61B 18/18
(52) U.S. Cl. ............................. 606/23; 606/20; 607/96
(58) Field of Search ........................ 606/20–25; 607/96, 607/104, 105, 113

(56) References Cited

U.S. PATENT DOCUMENTS

| 5,324,286 A | 6/1994 | Fowle | |
| 5,452,582 A | * 9/1995 | Longsworth | 606/24 |
| 5,520,682 A | * 5/1996 | Baust et al. | 606/20 |
| 5,885,276 A | * 3/1999 | Ammar et al. | 606/21 |

FOREIGN PATENT DOCUMENTS

WO 9714005 4/1997

* cited by examiner

Primary Examiner—Rosiland S. Kearney
(74) Attorney, Agent, or Firm—Dykema Gossett PLLC

(57) ABSTRACT

The invention relates to a cryoinstrument which is provided for carrying out cryosurgical interventions in the area of human and veterinary medicine, especially for treating tumors, and in the area of phytopathology and which is connected to a connecting device of a cryogenic appliance or system. The inventive cryoinstrument is comprised of a housing (1) in which a line is located that is provided for the direct flow (2) and for the return flow (3) of a cryogenic medium, e.g. liquid nitrogen. The housing has at least one closed end piece (4) which forms a working surface (5) with an exterior side (6) for cooling a tissue, and has a temperature sensor (7). In order to be able to constantly maintain the minimal temperature, in particular, between −40° C. and −196° C., with a low level of cryogenic medium loss on the working exterior side of the cryoinstrument which is in contact with the biological tissue, especially cancer tissue, the invention provides that an element is arranged in the housing (1) which has a porous structure (8) that is, for example, comprised of copper (cuprum) and whose degree of porosity and pore size, in a dimension ranging from approximately 10 μm to 15 μm, increases from the interior in a direction toward the exterior.

10 Claims, 5 Drawing Sheets

DEVICE FOR CARRYING OUT CRYOSURGICAL INTERVENTIONS, ESPECIALLY FOR TREATING TUMORS

BACKGROUND OF THE INVENTION

1. Field of the Invention

The invention relates to a cryogenic device useful in treating tumors.

2. The Prior Art

Cryosurgical instruments are mainly used in the treatment of cancer, the cryogenic instruments being applied onto the surface or inserted into the tumor tissue so that, as a result of the purposeful action of extreme cold temperatures, the diseased tissue is, to a great extent, destroyed or killed, and the biochemical as well as the biophysical processes are made locally irreversible. Smaller tumorous masses are thus destroyed and the cancer cells cannot proliferate any longer. This measure helps in preventing the local relapse as well as metastasis of cancer cells in small tumors. Further applications may be for example in general surgery, urology, gynecology, otorhinolaryngology and ophthalmology, plastic surgery, gnathosurgery, orthopaedics, veterinary medicine, also phytopathology, and so on.

A drawback to using these known cryogenic instruments, however, is that large amounts of tumor tissues are not destroyed completely.

Another disadvantage of the known devices is that the flow paths for the liquid cryogenic medium and the gaseous cryogenic medium are not separated, so that the flows of the different phases will affect each other. This makes it impossible to keep the minimum temperature constant on the exterior side of the working surface of the devices and to keep the loss of the cryogenic medium low.

It is therefore the object of the invention to improve on the known instruments so that large amounts of diseased tumour tissues are destroyed or killed as well and the biochemical as well as the biophysical processes become irreversible. The complete tumorous mass is thus destroyed and the cancer cells cannot proliferate any longer, so that local relapse (regrowth) of the tumor as well as metastasis of cancer cells is avoided with small and large tumors alike.

Additionally, and in order to keep the minimum temperature constant on the exterior side of the end piece of the instruments, the loss of the cryogenic medium is kept extremely low for cryogenic effect.

This is only made possible by reaching the minimum temperature and keeping it constant on the exterior working side of the cryogenic instrument contacting biological tissue.

The invention provides cryogenic instruments which are connected to a connecting device of a cryogenic apparatus or system and which are used for various application ranges.

The invention provides a cryogenic instrument designed as a cryoapplicator which, due to the uniform working surface, preferably in sizes between 3 mm and 55 mm, is convenient for the treatment of and can purposefully be applied to the large amount of tissue invaded, either on its surface or in its interior, by a tumor.

The invention provides a cryogenic instrument designed as a cryogenic needle which is preferably utilized for the treatment of diseased tissues located deep within the human body such as a liver tumor or a prostatic tumor.

The invention provides a cryogenic instrument designed as a cryoprobe for the treatment of tumors which grow into the healthy tissue, infiltrating in different ways, like, e.g., a soft tissue sarcoma.

The cryogenic instrument of the invention developed into a cryomammotome, is preferably used in the treatment of breast and prostate cancer.

Pedunculated tumors, polyps, e.g., are purposefully treated with the cryoclamp.

BRIEF DESCRIPTION OF THE DRAWINGS

The invention is described in greater detail with the help of the attached drawings wherein.

DETAILED DESCRIPTION OF THE PREFERRED EMBODIMENT

Figure 1:
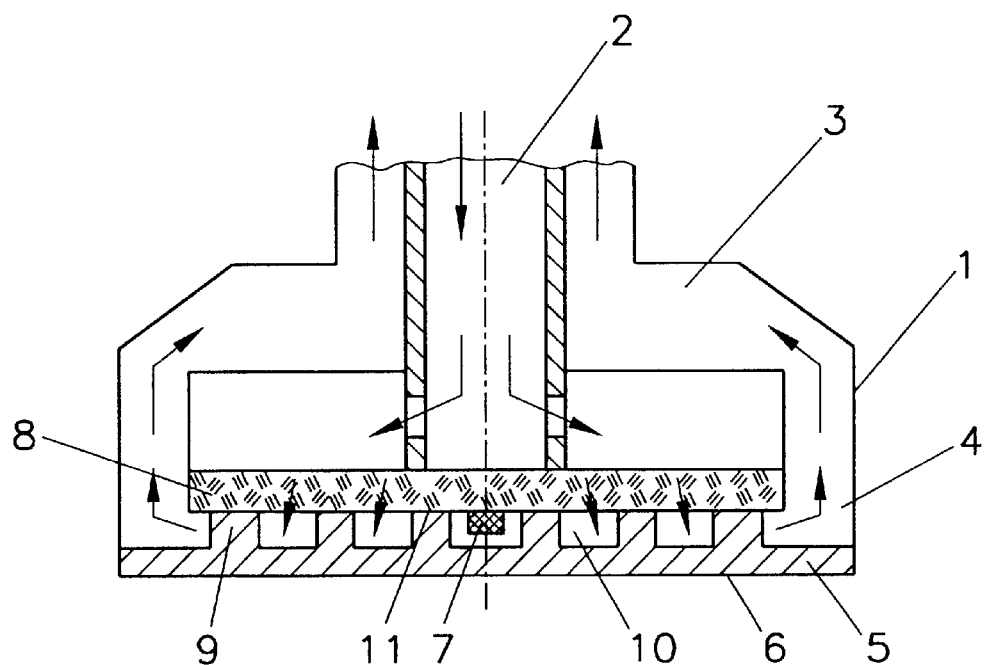
FIG. 1 shows a longitudinal section of a cryogenic instrument according to a preferred embodiment of the invention designed as a cryoapplicator.

The cryoinstruments of the invention are connected to a connecting device of a cryogenic apparatus or system, but this connecting device is not illustrated in the Figures herein.

The device for cryosurgical interventions consists of a housing (1) made of stainless steel which may have various shapes in cross section, for example round, in which there is one line for the direct flow (2) and one for the return flow (3) of a cryogenic medium, e.g., liquid nitrogen, with at least one closed end piece(4) which forms a working surface (5) with an exterior side (6) for cooling a tissue and consists of an oxygen-free, thermally conductive copper as well as with a temperature sensor (7).

In order to reach and keep the minimum temperature constant, more specifically between −40° C. and −196° C., with a low loss of the cryogenic medium at the exterior side (6) of the working surface of the end piece (4) of the cryoinstrument contacting biological tissue, more specifically cancerous tissue, an element with a porous structure (8), for example made of cuprum, is arranged in the housing (1).

The degree of porosity and the pore size, in the dimension ranging from approximately 10 $\mu$m to 15 $\mu$m, increase from the interior in a direction toward the exterior; as a result, the capillary forces of the porous structure (8) become stronger than the vapor pressure of the cryogenic medium that possibly evaporates on ribs (9). Only the evaporated cryogenic medium is evacuated, possibly through channels (10) between the ribs (9), into the cryogenic line (3) so that the liquid phase in the porous structure (8) is not affected.

The cryoapplicator (FIG. 1) consists of an end piece (4) evenly fitted with ribs that are arranged vertically on the inner side. Channels (10) form between the ribs (9) through which the evaporated cryogenic medium is returned into the cryogenic line (3).

On the inner side of the surface provided with ribs (9) an element with a porous structure (8) is welded according to the diffusion welding process. The structure (8) is formed by misoriented sections of copper wire which are welded together according to the diffusion welding process as well. The porosity ratio and the pore size are variable and the size is of approximately 10 $\mu$m to 15 $\mu$m; they become larger as they are located nearer to the rib edge (11). The liquid cryogenic medium is delivered to the porous structure (8), is absorbed and kept due to the capillary forces. Boiling of the fluid cryogenic medium and dissipation of heat from the biological tissue takes place at the boundary between the porous structure (8) and the edges of the ribs (9). Owing to the abovementioned porosity ratio and the pore size, the capillary forces become stronger than the vapor pressure so that the evaporated cryogenic medium alone is evacuated through the channels (10) between the ribs (9) into the cryogenic line (3). The liquid phase in the porous layer (8) is not affected thereby.

The housing (1) preferably has a round section and the end piece (4) is configured as a surface fitted with ribs arranged on the inner side, so that channels (10) for the passage of the evaporated cryogenic medium form between the ribs (9). A layer with the porous structure (8) is welded onto the surface.

The porous structure (8) is made of misoriented copper wire sections which are welded together according to the diffusion welding process.

The complete separation of the flow paths of the liquid cryogenic medium and the gaseous cryogenic medium as it has been realized by the invention and as it is illustrated in FIG. 1, together with the relatively small pore size of approximately 10 $\mu$m to 15 $\mu$m ensure an excellent transfer of heat, which makes it possible to have the temperature on the exterior side of the cryoinstrument (cryoapplicator) lying only slightly above the temperature of ebullition of the cryogenic medium. Owing to the arrangement of the porous structure (8) with pore sizes ranging from approximately 10 $\mu$m to 15 $\mu$m and less, the capillary forces get stronger than the vapour pressure of the cryogenic medium, so that the evaporated cryogenic medium alone is carried off through the channels (10) between the ribs (9) into the cryogenic line (3), and that the liquid cryogenic medium is kept in the lower layer of the porous structure (8). Hence, the liquid phase in the porous structure (8) is not affected.

By using misoriented copper sections welded together, a directed and clearly defined flow of the cryogenic medium is achieved within the porous material (8) as well.

Figure 2:
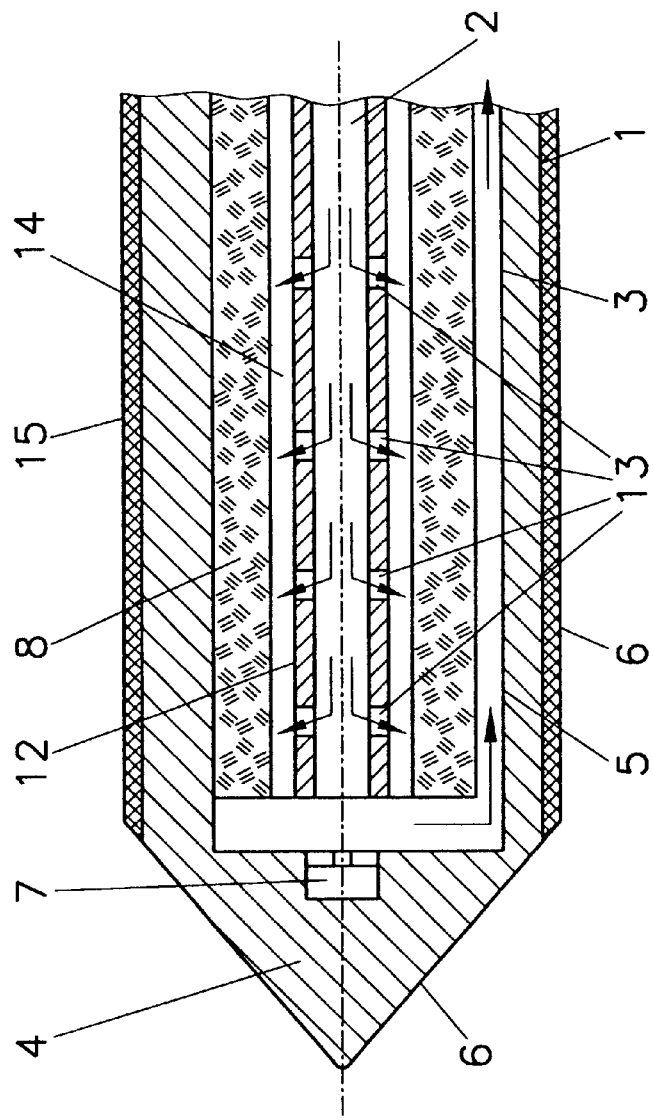
FIG. 2 shows a longitudinal section of another preferred embodiment designed as a cryoneedle as seen along line 2—2 of FIG. 3.
Figure 3:
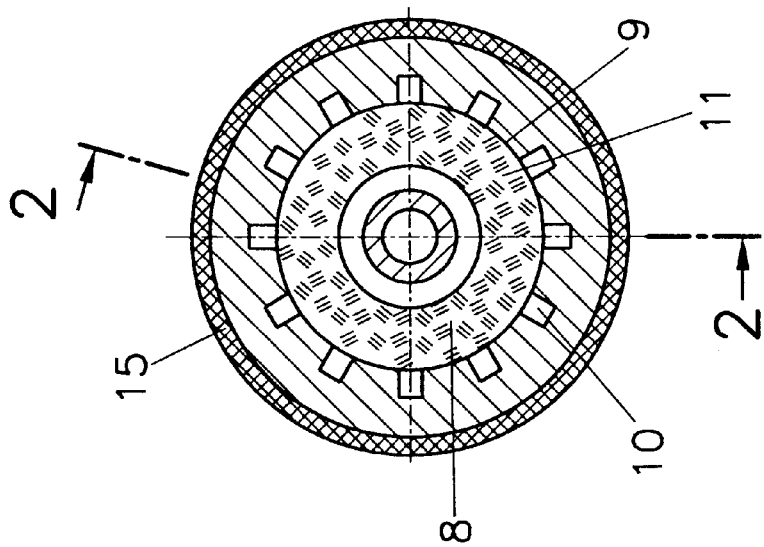
FIG. 3 shows a cross section of the cryoneedle of FIG. 2.

According to FIGS. 2 and 3, the cryoinstrument is designed as a hollow cryoneedle. The inner side (12) of the substantially cylindrical housing (1) is provided with ribs (9). The channels (10) are thus formed between the ribs (9) and serve for the exit of the evaporated cryogenic medium and a round layer with a porous structure (8) is welded on the ribs (9). The walls of the line (2) for the direct flow are provided in length, which length mates the freezing length of the cryoneedle, with a plurality of radial opposing exit openings (13) through which the cryogenic medium flows into the porous structure (8) after having passed a space (14) arranged between the wall of the line (2) for the direct flow and the porous structure (8), the through-flow through the porous structure (8) being thus essentially effected in radial direction so that the capillary forces of the porous structure (8) are stronger than the vapour pressure of the cryogenic medium evaporated on the ribs (9). The liquid phase of the porous structure (8) is not affected and a directed, clearly defined flow of the cryogenic medium is achieved within the porous material as well.

The line (2) within the porous structure (8) is arranged with play.

On its inner side, the housing (1) is provided with ribs (9) substantially extending in axial direction, channels (10) being designed therein between for returning the evaporated cryogenic medium.

In order to avoid the steam dome on the ribs (9) as transition from the liquid to the vapour state of the cryogenic medium takes place and to thus also permit a minimum temperature on the working surface of the substantially cylindrical cryoneedle, the working surface of the substantially cylindrical housing (1) of the cryoneedle is arranged from the exterior by means of a thermal insulation (15) consisting of a thin layer e.g., 0,2–0,7 mm in the cryoinstrument with a diameter of 4 mm of a thermally insulating material with a low thermal conductivity, e.g., stainless steel. The thickness of the layer depends upon the diameter of the cryoinstrument, i.e. the greater the diameter of the cryoneedle, the smaller the thickness of the layer is made. As a result, the condition for the transition state of the cryogenic medium is additionally achieved, the heat flow toward the cryogenic medium evaporated in the porous structure being reduced, which contributes to reach the minimum temperature.

Figure 4:
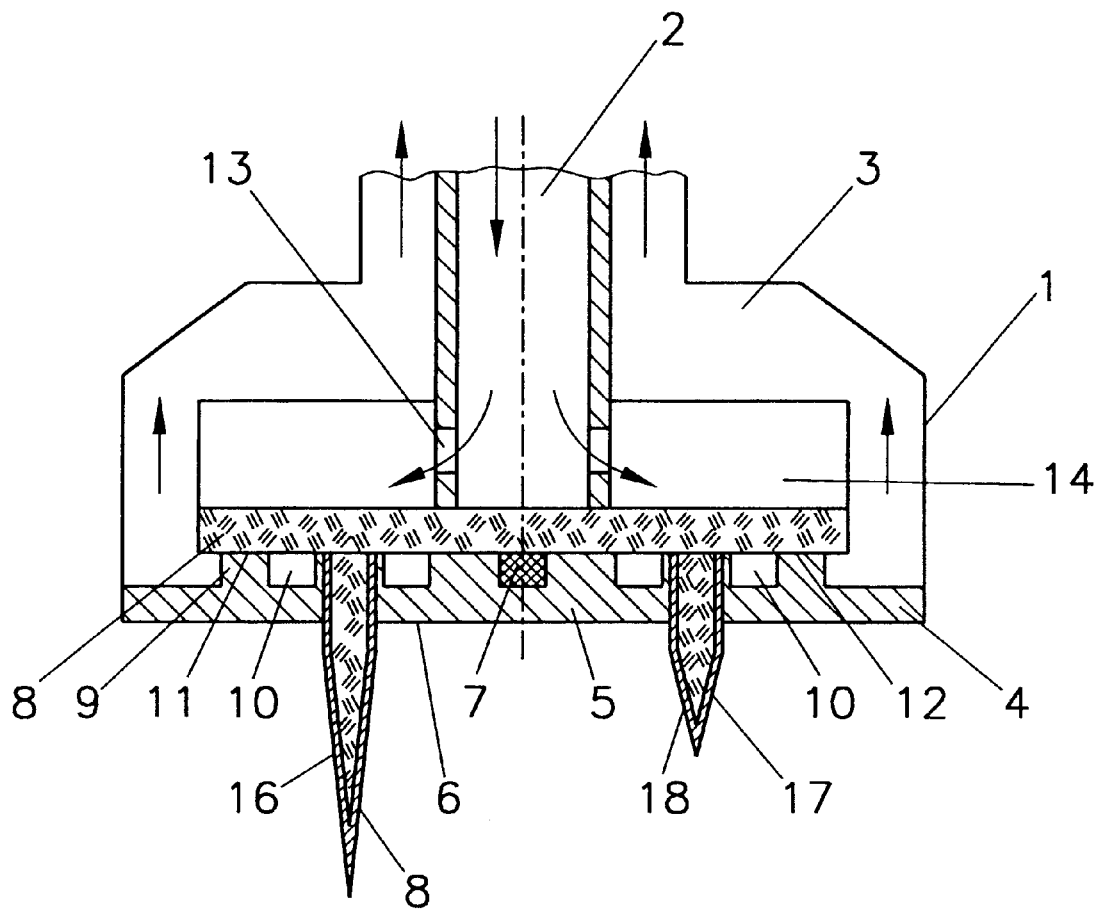
FIG. 4 shows a cross section of a cryoprobe.

The cryogenic instrument (FIG. 4) is designed as a cryoprobe which has elements (8) with the porous structure. The walls of the line (2) in the vicinity of the end piece (4) are provided with opposite passage holes (13) through which the cryogenic medium flows into a space (14). Notches (16) of a conical shape and of various length, ranging from 1 to 30 cm for example, and number, e.g., from 1 to 15, are arranged on the interior side of the end piece (4) and are provided within with a porous structure (8) and on the outside with an impermeable wall (17), whereas the notches (16) with screw thread (18) are removably fastened for the purpose of reaching and keeping constant the minimum temperature when in contact with diseased tissue not only located on the surface but also with such tissue located deep within the human body, the cryodestruction of the complete tumorous mass being thus made certain.

Figure 5:
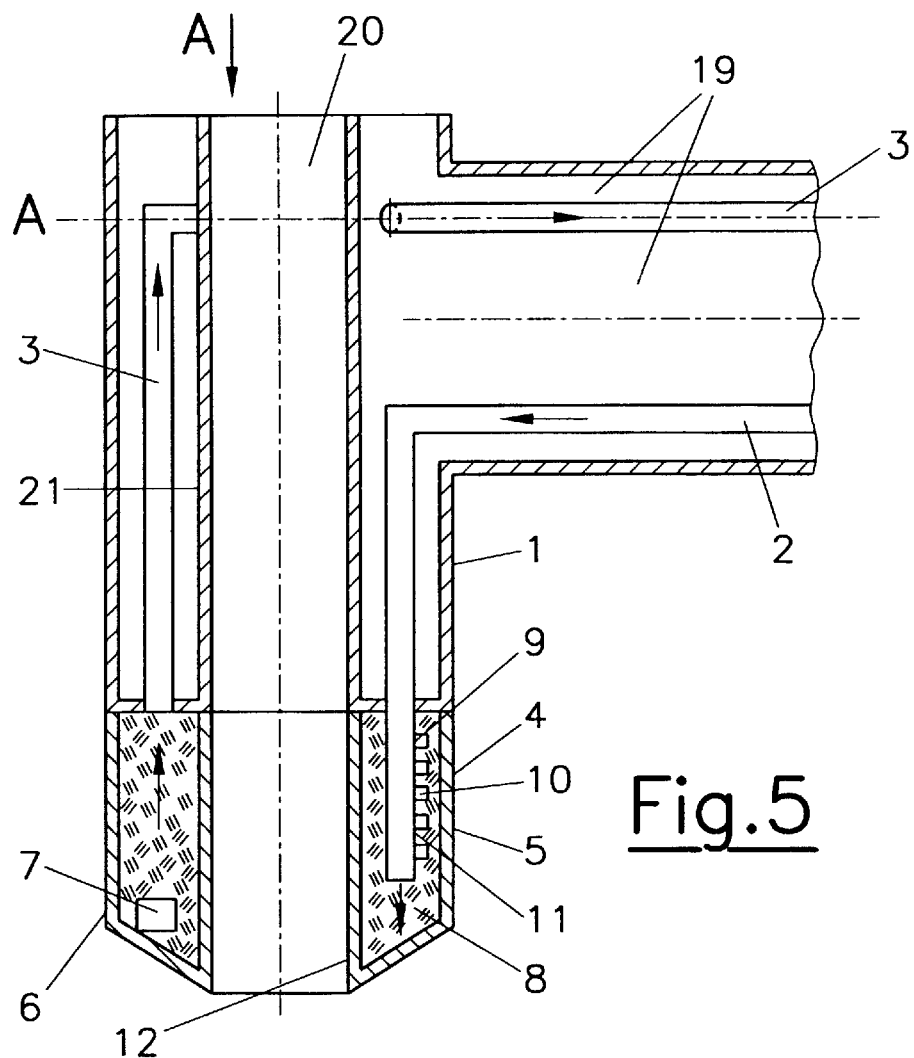
FIG. 5 shows a longitudinal section of a cryomammotome.
Figure 6:
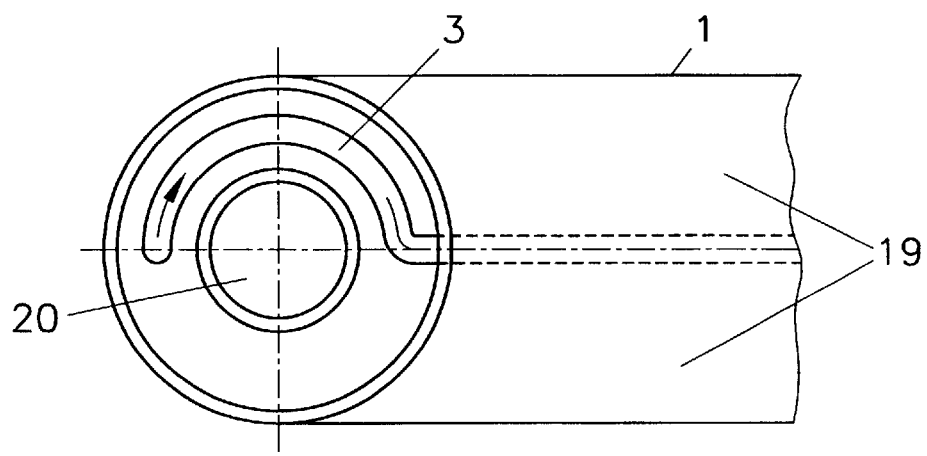
FIG. 6 shows a cryomammotome as seen along the line 6—6 of FIG. 5.
Figure 7:
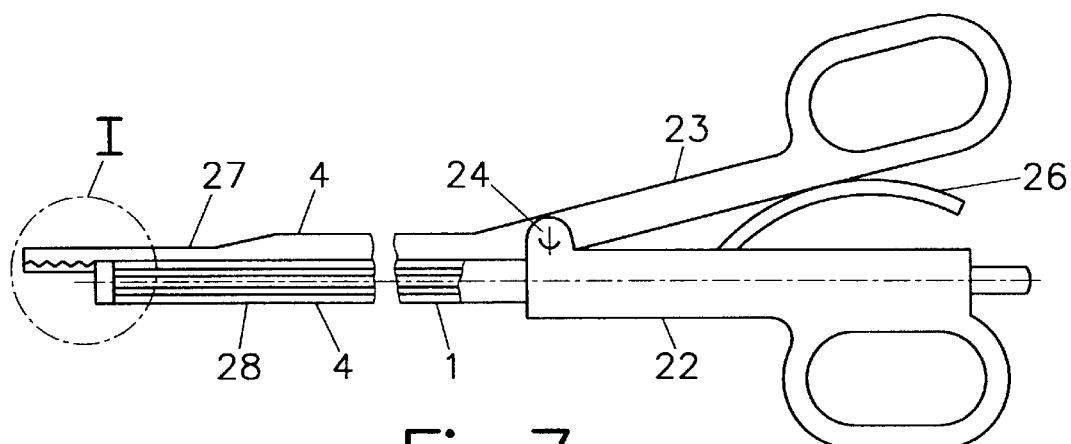
FIG. 7 shows a longitudinal section of a cryoclamp.
Figure 8:
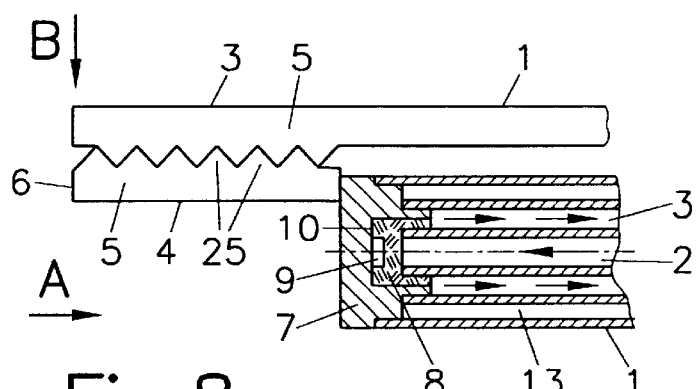
FIG. 8 shows a portion of FIG. 7—the tip of the cryoclamp.
Figure 9:
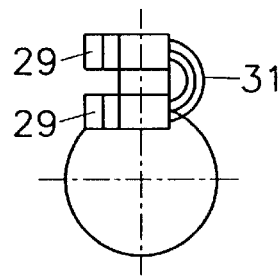
FIG. 9 shows a cross section (in the direction of arrow A) of a detail of FIG. 8.
Figure 10:
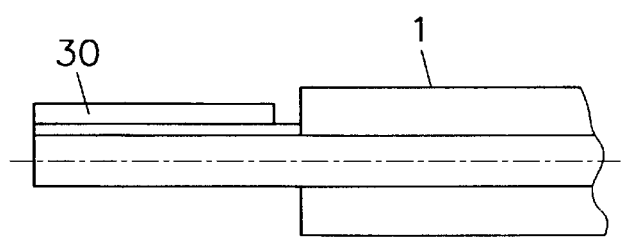
FIG. 10 shows a longitudinal section (in the direction of arrow B) of a detail of FIG. 8.

The cryogenic instrument (FIG. 5 and 6) is designed as a cryomammotome with the end piece (4) configured to form a cryotip, which is fitted in the housing (1) with a vacuum insulation (19), a heat-insulated channel (20) of a diameter of preferably 6 mm to 7 mm, with a thin wall (21) of preferably 0.2 mm to 0.3 mm made of stainless steel for biopsy and aspiration of the diseased tissue, more specifically of tissue from breast tumour. The housing (1) is manufactured under an angle of preferably 15° to 160°. The line (2) for the direct flow of the cryogenic medium leads into the element with porous structure (8). The inner side (12) of the cryotip (4) freezes a remnant of the diseased tissue which remains in the channel (20) as well as in the organ, e.g., in the breast, after aspiration. The line (3) for the return flow of the cryogenic medium is not connected with the element with porous structure (8) and surrounds the channel (20) describing a semicircle. The channel (20) is constantly kept free for various functions, more specifically for biopsy and aspiration of the diseased tissue.

According to FIGS. 7 to 10, the cryoinstrument is designed as a cryoclamp with a housing (1). The housing (1)

is arranged with an immovable and a movable branch (22, 23) which are connected to one another by a joint (24) and whose working surfaces (5) are fitted on their exterior side (6) with notches (25), wherein the housing (1) is made of stainless steel with low thermal conductivity and the branch (22, 23) of cuprum with high thermal conductivity. The cryoclamp additionally consists of a spring stopper (26) for the movable branch (23) as well as of a mouth with a movable and an immovable part (27, 28). A heat-insulated heater (29) is located on the inner side of the movable (27) and immovable (28) part of the mouth. A heat exchanger (30) is connected to the immovable part of the mouth (28), which is not provided with notches (25). A bridge (31), made of an elastic conductor of cold, configured as a wire having a diameter of preferably 4 to 8 mm and consisting of several strands of a diameter of preferably 20 to 60 $\mu$m of cuprum, is arranged between the heat exchanger (30) and the movable part of the mouth (28) for the purpose of dissipating the heat from the movable part of the mouth (27) into the heat exchanger (30). The line (2) for the direct flow of the cryogenic medium and the line (3) for the return flow of the cryogenic medium are arranged in the immovable part of the mouth (28) to fit the purpose of an accurate and certain cryodestruction of the pedunculated diseased tissue, more specifically of cancerous tissue in an anatomic region, e.g., the rectum, so that a relapse of the tumour is prevented and merely the neighbouring healthy structures are heated, thus sparing the healthy tissue.

What is claimed is:

1. Cryoinstrument for carrying out cryosurgical interventions in the area of human and veterinary medicine, especially for treating tumors, and in the area of phytopathology for connection to a connecting device of a cryogenic appliance or system, comprising a housing (1) in which there is located one line for the direct flow (2) and one line for the return flow (3) of a cryogenic medium with at least one closed end piece (4) which forms a working surface (5) with an exterior side (6) for cooling a tissue and internally-directed ribs (9) forming channels (10) therebetween, and with a temperature sensor (7), wherein in order to reach and keep the minimum temperature constant, with a low loss of the cryogenic medium on the working exterior side of the cryoinstrument which is in contact with biological tissue, an element with a porous structure (8) and whose degree of porosity and pore size, in the dimension of approximately 10 $\mu$m to 15 $\mu$m, increases from an interior in a direction toward the exterior, is arranged in the housing (1) so that the capillary forces of the porous structure (8) are greater than the vapour pressure of the cryogenic medium evaporated on the ribs (9) and that the evaporated cryogenic medium alone is evacuated through the channels (10) between the ribs (9) into the cryogenic line for the return flow (3), so that the liquid phase in the porous structure (8) is not affected.

2. Cryoinstrument according to claim 1, designed as a cryoapplicator, wherein the housing has a round section and the end piece (4) is configured as a surface which is fitted with ribs (9) arranged on the inner side and onto which a layer with the porous structure (8) is welded, so that channels (10) for the passage of the evaporated cryogenic medium are formed between the ribs.

3. Cryoinstrument according to claim 2, wherein the structure (8) is made of misoriented copper wire sections which are welded together according to a diffusion welding process.

4. Cryoinstrument according to claim 1, designed as a hollow cryoneedle, having a length of up to 150 mm and a width of 3 to 15 mm, wherein the inner side (12) of the substantially cylindrical housing (1) is provided with ribs (9) so that channels (10) are formed between the ribs and serve for the exit of the evaporated cryogenic medium and a round layer with a porous structure (8) is welded on the ribs (9) and the walls of the line (2) for the direct flow are provided in length, which length mates the freezing length of the cryoneedle, with a plurality of radial opposing exit openings (13) through which the cryogenic medium flows into the porous structure (8) after having passed a space (14) arranged between the wall of the line (2) for the direct flow and the porous structure (8).

5. Cryoinstrument according to claim 4, wherein the line (2) within the porous structure (8) is arranged with play.

6. Cryoinstrument according to claim 4 wherein the housing (1) is provided on its inner side (12) with ribs (9) substantially extending in an axial direction, channels (10) being designed therein between for returning evaporated cryogenic medium.

7. Cryoinstrument according to claim 4, wherein in order to avoid the steam dome on the ribs (9) as transition from the liquid to the vapor state of the cryogenic medium takes place and to thus also permit a minimum temperature on the working surface of the substantially cylindrical cryoneedle, the working surface of the substantially cylindrical housing (1) of the cryoneedle is provided from the exterior by means of a heat insulation (15) with a thin layer in the cryoinstrument with a diameter of 4 mm, wherein the thickness of the layer is smaller or greater as the diameter of the cryoneedle increases or decreases, and furthermore is made of a thermally insulating material with a low thermal conductivity in order to additionally achieve the condition for the transition state of the cryogenic medium, the heat flow toward the cryogenic medium evaporated in the porous structure (8) being reduced as a result, which contributes to reaching the minimum temperature.

8. Cryoinstrument according to claim 1, designed as a cryoprobe and wherein the elements (8) have a porous structure, wherein the walls of the line (2) in the vicinity of the end piece (4) are provided with opposite passage holes (13) through which the cryogenic medium flows into a space (14), that notches (16) of a conical shape and of various length, ranging from 1 to 30 cm, and from 1 to 15 in number, are arranged on the interior side (12) of the end piece (4) and are provided within with a porous structure (8) and on the outside with an impermeable wall (17), the notches (16) with screw thread (18) being removably fastened.

9. Cryoinstrument according to claim 1, designed as a cryomammotome with the end piece (4) configured to form a cryotip, which is fitted in the housing (1) with a vacuum insulation (19), a heat-insulated channel (20) of a diameter of 6 mm to 7 mm, with a thin wall (21) made of stainless steel for biopsy and aspiration of diseased tissue, more specifically of tissue from breast tumor, wherein moreover the housing (1) is manufactured under an angle of 15° to 160° and the line (2) for the direct flow of the cryogenic medium leads into the element with porous structure (8) so that the inner side (12) of the cryotip (4) freezes a remnant of the diseased tissue which remains in the channel (20) as well as in the organ after aspiration, wherein the line (3) for the return flow of the cryogenic medium is not connected with the element with porous structure (8) and surrounds the channel (20) describing a semicircle so that the channel (20) is constantly kept free for various functions, more specifically for biopsy and aspiration of the diseased tissue.

10. Cryoinstrument according to claim 1, designed as a cryoclamp with a housing (1) which is provided with an immovable and a movable branch (22, 23) which are connected to one another by a joint (24) and whose working surfaces (5) are fitted on their exterior side (6) with notches (25). as well as with a mouth with a movable and an immovable part (27, 28), wherein the line (2) for the direct flow of the cryogenic medium and the line (3) for the return flow of the cryogenic medium are arranged in the immovable part of the mouth, wherein a heat-insulated heater (29) is located on the inner side of the movable (27) and immovable (28) part of the mouth and wherein the immovable part of the mouth (28), which is not provided with notches (25), is connected to a heat exchanger (30) so that a bridge (31), made of an elastic conductor of cold, configured as a wire having a diameter of 4 to 8 mm and consisting of several strands of a diameter of 20 to 60 $\mu$m of cuprum, is arranged between the heat exchanger (30) and the movable part of the mouth (27).

\* \* \* \* \*